US012691075B2

(12) United States Patent
Luedecke et al.

(10) Patent No.: US 12,691,075 B2
(45) Date of Patent: Jul. 28, 2026

(54) ENTERIC COATING COMPOSITION AND METHOD OF MAKING AND USING THE SAME

(71) Applicant: Sensient Colors LLC, St. Louis, MO (US)

(72) Inventors: Steven Luedecke, St. Louis, MO (US); Houston Smith, St. Louis, MO (US)

(73) Assignee: Sensient Colors LLC, St. Louis, MO (US)

( * ) Notice: Subject to any disclaimer, the term of this patent is extended or adjusted under 35 U.S.C. 154(b) by 569 days.

(21) Appl. No.: 18/012,386

(22) PCT Filed: Jun. 28, 2021

(86) PCT No.: PCT/US2021/039361
§ 371 (c)(1),
(2) Date: Dec. 22, 2022

(87) PCT Pub. No.: WO2021/263230
PCT Pub. Date: Dec. 30, 2021

(65) Prior Publication Data
US 2023/0263739 A1 Aug. 24, 2023

Related U.S. Application Data

(60) Provisional application No. 63/044,466, filed on Jun. 26, 2020.

(51) Int. Cl.
| | |
|---|---|
| *A61K 9/48* | (2006.01) |
| *A23L 29/10* | (2016.01) |
| *A23L 29/231* | (2016.01) |
| *A23L 29/256* | (2016.01) |
| *A23L 29/30* | (2016.01) |
| *A23P 20/10* | (2016.01) |
| *A61K 47/10* | (2017.01) |
| *A61K 47/36* | (2006.01) |
| *A61K 47/44* | (2017.01) |

(52) U.S. Cl.
CPC ............ *A61K 9/4891* (2013.01); *A23L 29/10* (2016.08); *A23L 29/231* (2016.08); *A23L 29/256* (2016.08); *A23L 29/30* (2016.08); *A23L 29/37* (2016.08); *A23P 20/105* (2016.08); *A61K 9/4825* (2013.01); *A61K 47/10* (2013.01); *A61K 47/36* (2013.01); *A61K 47/44* (2013.01)

(58) Field of Classification Search
CPC .... A61K 9/4891; A61K 9/4825; A61K 47/10; A61K 47/36; A61K 47/44; A61K 31/732; A61K 31/734; A61K 47/12; A61K 47/24; A61K 47/38; A23L 29/10; A23L 29/231; A23L 29/256; A23L 29/30; A23L 29/37; A23L 33/115; A23L 33/125; A23P 20/105
See application file for complete search history.

(56) References Cited

U.S. PATENT DOCUMENTS

| | | | |
|---|---|---|---|
| 9,629,802 B2 | 4/2017 | Young | |
| 10,206,881 B2 * | 2/2019 | Wright et al. | |
| 2003/0124196 A1 | 7/2003 | Weinback et al. | |
| 2011/0269850 A1 | 11/2011 | Signorino et al. | |

FOREIGN PATENT DOCUMENTS

| | | |
|---|---|---|
| WO | 2013155430 A1 | 10/2013 |
| WO | 2014136857 A1 | 9/2014 |
| WO | 2017187194 A1 | 11/2017 |
| WO | WO2017187194 * | 11/2017 |
| WO | 2021263230 A1 | 12/2021 |

OTHER PUBLICATIONS

Thermal, Mechanical and Rheological properties of plasticized poly (L-lactic acid) to Ge et al. (Year: 2012).*
Ge et al. "Thermal, Mechanical, and Rheological Properties of Plasticized Poly(L-lactic acid)" J. Appl. Polym. Sci. 2013, pp. 2832-2839.
International Search Report and Written Opinion issued in corresponding PCT Application No. PCT/US2021/039361, mailed Oct. 4, 2021.
"European Application Serial No. 21828843.9, Extended European Search Report mailed Jul. 1, 2024", Sensient Technologies Corporation, 7 pages.
"International Application Serial No. PCT/US2021/039361 , International Preliminary Report on Patentability mailed Dec. 13, 2022", Sensient Technologies Corporation, 6 pages.

* cited by examiner

*Primary Examiner* — Robert A Wax
*Assistant Examiner* — Kimberly Barber
(74) *Attorney, Agent, or Firm* — GTC Law Group PC & Affiliates

(57) ABSTRACT

A dosage form coating composition is disclosed. The composition includes an alginate, a pectin, a plasticizer, and optionally an emulsifying agent. The alginate is present in an amount by weight of at least 40.0% and at most 80.0% and the pectin is present in an amount by weight of at least 16.0% and at most 40.0%—and/or—the alginate and the pectin are present in a weight ratio of at least 1:1 and at most 5:1. The dosage form coating composition, when applied to a dosage form to a 3% to 5% weight gain, provides a coated dosage form having an enteric coating. The coated dosage form has at least two sequentially observed properties exhibiting enteric coating behavior.

20 Claims, No Drawings

ENTERIC COATING COMPOSITION AND METHOD OF MAKING AND USING THE SAME

CROSS-REFERENCE TO RELATED APPLICATIONS

This application is a national stage application filed under 35 U.S.C. § 371 of International Application No. PCT/US2021/039361, filed Jun. 28, 2021, which claims priority to, and incorporates by reference herein for all purposes U.S. Provisional Patent Application No. 63/044,466, filed Jun. 26, 2020.

BACKGROUND

Enteric coatings are known in the art to have the ability to endure the stomach's acidic environment and dissolve in the more neutral environment of the intestine. However, the variety of compositions and the ingredients contained therein are limited.

Most enteric coatings and enteric coating compositions traditionally involve the use of materials like shellac, cellulose-based materials, or modified food starches.

A need exists for additional compositions for making enteric coatings, which utilize a wider range of materials while maintaining enteric coating performance.

BRIEF SUMMARY

In an aspect, the present disclosure provides a dosage form coating composition. The dosage form coating composition include an alginate, a pectin and a plasticizer. The composition optionally include an emulsifying agent. The alginate is present in an amount by weight of at least 40.0% and at most 80.0%. The pectin is present in an amount by weight of at least 16.0% and at most 40.0%. The plasticizer is present in an amount by weight of at least 0.5% and at most 30.0%. The emulsifying agent, when optionally present, in present in an amount by weight of at least 0.1% and at most 10.0%. The dosage form coating composition, when applied to a dosage form to a 3% to 5% weight gain, provides a coated dosage form having an enteric coating. The coated dosage form has at least the following two sequentially observed properties: (i) the enteric coating does not exhibit visible signs of dissolution after being immersed in a 0.1 M solution of hydrochloric acid or simulated gastric fluid at a predetermined temperature and for a first predetermined length of time, wherein the predetermined temperature is between 30° C. and 45° C., wherein the first predetermined length of time is between 15 minutes and 3 hours; and (ii) after the being immersed in the 0.1 M solution of hydrochloric acid or simulated gastric fluid, the enteric coating is at least partially dissolved after being immersed in a phosphate buffer having a pH between 6.5 and 7.0 or simulated intestinal fluid at the predetermined temperature for a second predetermined length of time, wherein the second predetermined length of time is between 60 minutes and 6 hours.

In another aspect, the present disclosure provides a dosage form coating composition. The dosage form coating composition include an alginate, a pectin and a plasticizer. The composition optionally include an emulsifying agent. The alginate and the pectin are present in a weight ratio of at least 1:1 and at most 5:1. The dosage form coating composition, when applied to a dosage form to a 3% to 5% weight gain, provides a coated dosage form having an enteric coating. The coated dosage form has at least the following two sequentially observed properties: (i) the enteric coating does not exhibit visible signs of dissolution after being immersed in a 0.1 M solution of hydrochloric acid or simulated gastric fluid at a predetermined temperature and for a first predetermined length of time, wherein the predetermined temperature is between 30° C. and 45° C., wherein the first predetermined length of time is between 15 minutes and 3 hours; and (ii) after the being immersed in the 0.1 M solution of hydrochloric acid or simulated gastric fluid, the enteric coating is at least partially dissolved after being immersed in a phosphate buffer having a pH between 6.5 and 7.0 or simulated intestinal fluid at the predetermined temperature for a second predetermined length of time, wherein the second predetermined length of time is between 60 minutes and 6 hours.

In yet another aspect, the present disclosure provides a dosage form coating suspension. The dosage form coating suspension can include the dosage form coating composition as described herein and a solvent.

In a further aspect, the present disclosure provides a method of using the dosage form coating suspensions described herein. The method can include applying the dosage form coating suspension to an uncoated dosage form.

In another aspect, the present disclosure provides a method of making the dosage form coating compositions described herein. The method can include combining ingredients of the dosage form coating composition.

In yet another aspect, the present disclosure provides a coating. The coating can include non-volatile ingredients of the dosage form coating compositions described herein.

In a further aspect, the present disclosure provides a coated dosage form. The coated dosage form can include a dosage form and the coatings described herein.

DETAILED DESCRIPTION

Before the present invention is described in further detail, it is to be understood that the invention is not limited to the particular embodiments described. It is also to be understood that the terminology used herein is for the purpose of describing particular embodiments only, and is not intended to be limiting. The scope of the present invention will be limited only by the claims. As used herein, the singular forms "a", "an", and "the" include plural embodiments unless the context clearly dictates otherwise.

It should be apparent to those skilled in the art that many additional modifications beside those already described are possible without departing from the inventive concepts. In interpreting this disclosure, all terms should be interpreted in the broadest possible manner consistent with the context. Variations of the term "comprising", "including", or "having" should be interpreted as referring to elements, components, or steps in a non-exclusive manner, so the referenced elements, components, or steps may be combined with other elements, components, or steps that are not expressly referenced. Embodiments referenced as "comprising", "including", or "having" certain elements are also contemplated as "consisting essentially of" and "consisting of" those elements, unless the context clearly dictates otherwise. It should be appreciated that aspects of the disclosure that are described with respect to a system are applicable to the methods, and vice versa, unless the context explicitly dictates otherwise.

Numeric ranges disclosed herein are inclusive of their endpoints. For example, a numeric range of between 1 and 10 includes the values 1 and 10. When a series of numeric ranges are disclosed for a given value, the present disclosure expressly contemplates ranges including all combinations of the upper and lower bounds of those ranges. For example, a numeric range of between 1 and 10 or between 2 and 9 is intended to include the numeric ranges of between 1 and 9 and between 2 and 10.

The present disclosure provides a dosage form coating composition. The dosage form coating composition includes an alginate, a pectin, and a plasticizer. The composition optionally includes an emulsifying agent. The composition, when applied to a dosage form to a 3% to 5% weight gain, provides a coated dosage form having an enteric coating with at least one of the enteric properties described herein.

The alginate and the pectin can be present in a weight ratio of at least 1:1 and at most 5:1, including but not limited to, a weight ratio of at least 10:9, at least 9:8, at least 8:7, at least 7:6, at least 6:5, at least 5:4, at least 4:3, at least 3:2, at least 2:1, at least 3:1, or at least 4:1, or a weight ratio of at most 4:1, at most 35:9, at most 31:8, at most 27:7, at most 23:6, at most 19:5, at most 15:4, at most 11:3, at most 7:2, at most 3:1, or at most 2:1.

The alginate can be present in the dosage form coating composition in an amount by weight of at least 40.0% and at most 80.0%, including but not limited to, an amount by weight of at least 42.5%, at least 45.0%, at least 47.5%, at least 50.0%, at least 52.5%, at least 55.0%, at least 57.5%, at least 60.0%, at least 62.5%, at least 65.0%, at least 70.0%, or at least 75.0%, or an amount by weight of at most 77.5%, at most 75.0%, at most 72.5%, at most 70.0%, at most 67.5%, at most 65.0%, at most 62.5%, at most 60.0%, at most 57.5%, at most 55.0%, at most 52.5%, at most 50.0%, or at most 45.0%.

The alginate can be sodium alginate, though other alginates are contemplated to function in the dosage form coating composition. Without wishing to be bound by any particular theory, it may be advantageous to utilize a low viscosity sodium alginate in the dosage form coating composition.

The alginate can have a viscosity as measured at 10% solids of at least 1 cP, at least 5 cP, at least 10 cP, at least 25 cP, at least 50 cP, or at least 100 cP and at most 500 cP, at most 450 cP, at most 400 cP, at most 350 cP, at most 325 cP, or at most 300 cP. An example of a suitable alginate for use in the present disclosure includes, but is not limited to, Ultra Low Viscosity Sodium Alginate, available commercially from Qingdao Hyzlin Biology Development Co., Ltd., Qingdao, China. Viscosities described herein are measured using US Pharmacopeia chapter <912> Method 1 from the Second Supplement to USP 35-NF 30, the contents of which are hereby incorporated by reference for all purposes, using a rotational rheometer such as Brookfield DV2 T spindle rheometer, available commercially from AMETEK Brookfield, Middleboro, Mass.

The pectin can be present in the dosage form coating composition in an amount by weight of at least 16.0% or at most 40.0%, including but not limited to, an amount by weight of at least 17.0%, at least 18.0%, at least 19.0%, at least 20.0%, at least 21.0%, at least 22.0%, at least 23.0%, at least 24.0%, at least 25.0%, at least 30.0%, or at least 35.0%, or an amount by weight of at most 37.5%, at most 35.0%, at most 32.5%, at most 30.0%, at most 29.0%, at most 28.0%, at most 27.0%, at most 26.0%, at most 25.0%, at most 22.5%, or at most 20.0%. The pectin can have a degree of esterification of between 40% and 55%, including but not limited to, a degree of esterification of at least 40%, at least 42%, at least 44%, at least 45%, at least 47%, or at least 48%, or a degree of esterification of at most 55%, at most 54%, at most 53%, at most 52%, at most 51%, or at most 50%.

In some cases, the amount of alginate and the amount of pectin meet either the ratio limitations disclosed herein or the percent by weight values disclosed herein, and in some cases, they meet both.

The plasticizer can be present in an amount by weight of at least 0.5% and at most 30.0%, including but not limited to, an amount by weight of at least 2.5%, at least 5.0%, at least 7.5%, at least 10.0%, at least 12.5%, at least 15.0%, at least 20.0%, or at least 25.0%, or an amount by weight of at most 25.0%, at most 20.0%, at most 17.5%, at most 15.0%, or at most 10.0%.

The plasticizer can be any plasticizer that does not significantly alter the enteric coating properties of the compositions. The type of plasticizer and amount can be selected based on the desired viscosity of a resulting coating suspension. In some cases, the plasticizer can be glycerine (also called glycerol or glycerin).

The emulsifying agent can optionally be present in an amount by weight of at least 0.1% and at most 10.0%, including but not limited to, an amount by weight of at least 0.5%, at least 1.0%, at least 1.5%, at least 2.0%, at least 2.5%, at least 3.0%, at least 4.0%, at least 5.0%, or at least 7.5%, or an amount by weight of at most 9.0%, at most 8.0%, at most 7.0%, at most 6.0%, at most 5.0%, at most 4.0%, or at most 2.5%.

The emulsifying agent can be any emulsifying agent that does not significantly alter the enteric coating properties of the compositions. The type of emulsifying agent and amount can be selected based on the desired properties of a resulting coating suspension. In some cases, the emulsifying agent is a lecithin, such as sunflower lecithin.

The dosage form coating composition can include an opacifying agent.

The opacifying agent can be selected from the group consisting of titanium dioxide, calcium carbonate, Sensient® Avalanche™ (available commercially from Sensient Colors LLC, St. Louis, Mo.), other ingredients rendering opacification, and combinations thereof.

The dosage form coating composition can include a sweetening agent.

The sweetening agent can be selected from the group consisting of a sugar alcohol, an artificial sweetener, a natural sweetener, such as stevia, a sugar, and combinations thereof.

The sugar alcohol can be selected from the group consisting of sorbitol, mannitol, xylitol, isomalt, hydrogenated starch hydrolysates, and combinations thereof.

The artificial sweetener can be selected from the group consisting of sucralose, acesulfame, aspartame, and combinations thereof.

The sugar can be selected from the group consisting of sucrose, fructose, and combinations thereof.

The dosage form coating composition can include a flavorant or sensate. The flavorant can be a spray dried flavorant, a dried crystal flavorant, a granule flavorant, a liquid flavorant, or a combination thereof. The spray dried flavorant, the dried crystal flavorant, the granule flavorant, the liquid flavorant, or the combination thereof can comprise a synthetic flavoring agent, an artificial flavoring agent, a natural flavoring agent, or a combination thereof. The spray dried flavorant, the dried crystal flavorant, the granule flavorant, the liquid flavorant, or the combination thereof can provide a flavor selected from the group consisting of almond, amaretto, apple, green apple, apple-cherry-berry, apple-honey, apricot, bacon, banana, barbeque, beef, roast beef, beef steak, berry, berry blue, birch beer, spruce beer, blackberry, bloody mary, blueberry, boysenberry, brandy, bubble gum, butter, butter pecan, buttermilk, butterscotch, candy corn, cantaloupe, cantaloupe lime, caramel, carrot, cassia, caviar, celery, cereal, champagne, cherry, cherry cola, cherry maraschino, wild cherry, black cherry, red cherry, cherry-cola, chicken, chocolate, chocolate almond, cinnamon spice, citrus, citrus blend, citrus-strawberry, clam, cocoa, coconut, toasted coconut, coffee, coffee almond, cola, cola-vanilla, cookies & cream, cotton candy, cranberry, cranberry-raspberry, cream, cream soda, dairy type cream, creme de menthe, cucumber, black currant, dulce de leche, egg nog, pork fat, non-pork fat, anchovy fish, herring fish, sardine fish, frankfurter, fried garlic, sauteed garlic, gin, ginger ale, ginger beer, graham cracker type, grape, grape grapefruit, grapefruit-lemon, grapefruit-lime, grenadine, grill, guarana, guava, hazelnut, honey, roasted honey, ice cream cone, jalapeno, key lime, kiwi, kiwi-banana, kiwi-lemon-lime, kiwi-strawberry, kola champagne, lard type, lemon, lemon custard, lemonade, pink lemonade, lemon-lime, lime, malt, malted milk, mango, mango-pineapple, maple, margarita, marshmallow, meat type, condensed milk, cooked milk, mint, mirepoix, mocha, mochacinna, molasses, mushroom, sauteed mushroom, muskmelon, nectarine, neapolitan, green onion, sauteed onion, orange, orange cordial, orange creamsicle, orange creme, orange peach mango, orange strawberry banana, creamy orange, mandarin orange, orange-passion-guava, orange-pineapple, papaya, passion fruit, peach, peach-mango, peanut, roasted peanut, pear, pecan danish, pecan praline, pepper, peppermint, pimento, pina colada, pina colada/pineapple-coconut, pineapple, pineapple-orange, pistachio, pizza, pomegranate, baked potato, prune, punch, citrus punch, tropical punch, cherry fruit punch, grape punch, raspberry, black raspberry, blue raspberry, red raspberry, raspberry-blackberry, raspberry-ginger ale, raspberry-lime, root beer, rum, sangria, sarsaparilla, sassafras, sausage, sausage pizza, seafood, shrimp, hickory smoke, mesquite smoke, sour, sour cream, sour cream and onion, spearmint, strawberry, strawberry margarita, jam type strawberry, strawberry-kiwi, burnt sugar, tallow, tamarind, tangerine-lime, tangerine, tea, tequila, toffee, triple sec, tropical fruit mix, turkey, tutti frutti, vanilla, vanilla cream, vanilla custard, french vanilla, vegetable, vermouth, vinegar, balsamic vinegar, watermelon, whiskey, wildberry, wine, yogurt, and combinations thereof. The flavors described herein can be use alone or in combination with sensates described herein for experiential sensations of cooling, heating and tingling effects, such as use in combination with Sensient® Smoothenol® products.

The dosage form coating composition can include a sensate. The sensate can be a spray dried sensate, a dried crystal sensate, a granule sensate, a liquid sensate, or a combination thereof. The spray dried sensate, the dried crystal sensate, the granule sensate, the liquid sensate, or a combination thereof can provide a hot sensation, a cool sensation, a tingling sensation, or a combination thereof. In some cases, the sensate can be combined with a flavorant to provide a combination flavorant and sensate that combined the flavors and the sensations disclosed herein. In the event that a flavorant is combined with a sensate, the combination flavorant and sensate should be present in an amount that is equal to the amounts described herein with respect to flavorants and sensates.

The dosage form coating composition can include a flavor masking agent. The flavor masking agent can be selected from the group consisting of Smoothenol®, Smoothenol 2G® or numerical G Smoothenol®; such as 3G, 4G and in the forms of BitterFix™, AstringentFix™ FunctionalFix™, BurnFix™, SourFix™ (all available commercially from Sensient Flavors LLC, Hoffman Estates, Ill.), and combinations thereof. In some cases, the flavor masking agent can be combined with a flavorant, a sweetener, a sweetener enhancer, or the like. In some cases, the flavor masking agent can be contained in a combination product, such as Mafco's Magnasweet® line of products (available commercially from MAFCO Worldwide LLC, Camden, N.J.).

The dosage form coating composition can include a colorant. The colorant can be selected from the group consisting of a pigment, a dye, an exempt colorant (i.e., a colorant from a natural source), and combinations thereof.

The dosage form coating composition can be substantially free of various components that are commonly used in the dosage form enteric coating arts. The dosage form coating composition can be substantially free of methyl acrylate copolymers, acrylate copolymers, or a combination thereof, such as methyl acrylate-acrylate copolymer. The dosage form coating composition can be substantially free of methyl acrylate emulsion. The dosage form coating composition can be substantially free of polymer phthalates, such as cellulose acetate phthalate (CAP), hydroxypropyl methyl cellulose phthalate (HMPCP), polyvinyl acetate phthalate (PVAP), or combinations thereof. The dosage form coating composition can be substantially free of cellulose acetate phthalate (CAT). The dosage form coating composition can be substantially free of cellulosic film formers, such as hydroxypropyl methyl cellulose (HPMC), ethyl cellulose, carboxymethyl cellulose (CMC), sodium carboxymethyl cellulose (NaCMC), methyl cellulose, or combinations thereof. The dosage form coating composition can be substantially free of shellac. The dosage form coating composition can be substantially fee of modified food starch or modified plant starch.

The present disclosure provides a dosage form coating suspension. The dosage form coating suspension can include the dosage form coating composition, as described elsewhere herein, and a solvent. The solvent can be water.

The dosage form coating suspension can have a solids content of at least 5.0%, at least 8.5%, at least 9.0%, at least 9.5%, at least 10.0%, at least 10.5%, or at least 11.0%. The dosage form coating suspension can have a solids content of at most 13.0%, at most 12.5%, at most 12.0%, at most 11.5%, at most 11.0%, at most 10.5%, or at most 10.0%.

The dosage form coating suspension can have a viscosity of between 10 cP and 2000 cP, including but not limited to, between 500 cP and 1000 cP. In some cases, the viscosity can be at least 10 cP, at least 100 cP, at least 200 cP, at least 250 cP, at least 300 cP, at least 375 cP, at least 400 cP, at least 450 cP, or at least 500 cP. In some cases, the viscosity can be at most 2000 cP, at most 1750 cP, at most 1500 cP, at most 1350 cP, at most 1250 cP, at most 1200 cP, at most 1100 cP, at most 1000 cP, at most 900 cP, at most 850 cP, at most 750 cP, at most 600 cP, or at most 500 cP. In some cases, the viscosity can be represented as the viscosity measured at 10% solids (i.e., two coating suspensions formed from the same coating composition but with different solids contents would have the same viscosity). In other cases, the viscosity can be represented as the viscosity measured at the specific solids content of the coating suspension (i.e., two coating suspensions formed from the same coating composition but with different solids contents would have different viscosities).

The present disclosure provides a coating. The coating is the result of applying the dosage form coating suspension to an article in accordance with the methods described herein. The coating can include the same or substantially similar components as described elsewhere herein with respect to the dosage form coating composition, minus any volatile components that are removed in the coating process, as would be understood by a person having ordinary skill in the art.

The present disclosure provides a coated dosage form. The coated dosage form is the result of applying the dosage form coating suspension to a dosage form in accordance with the methods described herein. The coated dosage form includes the dosage form and the coating, as described elsewhere herein. The composition can be used to coat a wide variety of dosage forms, including but not limited to, tablets, caplets, capsules, softgels, dissolvable strips, multi-particulates, and the like.

The coating and the coated dosage form are both capable of passing the USP 32 chapter <701> and/or chapter <2040> tests. A person having ordinary skill in the art would understand how to locate the instructions for conducting these tests and to conduct said testing. Nonetheless, USP 32 chapter <701> and chapter <2040> are incorporated herein in their entirety by reference. Briefly, each of these tests involves a 6 chamber experiment for testing 6 different dosage forms. Six open-topped containers are immersed in a thermal bath. A testing solution can be added to these containers. Six baskets are introduced into the containers, one for each container, and raised and lowered at a predetermined rate. During a first part of the test the containers include 0.1 M hydrochloric acid solutions or simulated gastric fluid TS. A coated dosage form is introduced into each of the baskets. The dosage form is lowered into the solution/fluid and raised and lowered at a predetermined rate to ensure movement of the fluid, but without any abrupt or agitating movements. The first part requires 60 minutes of immersion. After the first part, the second part of the test involves a phosphate buffer with a pH of 6.8 or simulated intestinal fluid TS. The same immersion process from the first part is repeated with the phosphate buffer or the simulated intestinal fluid.

A partial dissolution in the first part of the test is considered a failing result and at least partial dissolution in the second part of the test is required for a passing result.

In some cases, a coating or an enteric coating as disclosed herein can exhibit no visible signs of dissolution after being immersed in a 0.1 M solution of hydrochloric acid or simulated gastric fluid at a predetermined temperature and for a first predetermined length of time. In some cases, after this immersion, a coating or an enteric coating as disclosed herein is at least partially dissolved after being immersed in a phosphate buffer having a pH between 6.5 and 7.0 or simulated intestinal fluid at the predetermined temperature for a second predetermined length of time. The first predetermined length of time is between 15 minutes and 3 hours, and in some cases, is 60 minutes. The second predetermined length of time is between 60 minutes and 6 hours, and in some cases, is 60 minutes. The predefined temperature can be between 30° C. and 45° C. or between 35° C. and 39° C.

As used herein, "simulated gastric fluid TS" or "simulated gastric fluid" refers to a fluid made with the process described in this paragraph. Dissolve 2.0g of sodium chloride and 3.2g of purified pepsin, which is derived from porcine stomach mucosa, with an activity of 800 to 2500 units per mg of protein, in 7.0 mL of hydrochloric acid and sufficient water to make 1000 mL. The resulting pH should be approximately 1.2.

As used herein, "simulated intestinal fluid TS" or "simulated intestinal fluid" refers to a fluid made with the process described in this paragraph. Dissolve 6.8g of monobasic potassium phosphate in 25 0 mLof water, mix, and add 77 mL of 0.2 N sodium hydroxide and 500 mL of water. Add 10.0 g of pancreatin, mix, and adjust the resulting solution with either 0.2 N sodium hydroxide or 0.2 N hydrochloric acid to a pH of 6.8±0.1. Dilute with water to 1000 mL.

The present disclosure provides a method of making a dosage form coating composition and/or suspension.

The method of making the dosage form composition can include combining and/or mixing the various components of the dosage form coating composition.

The method of making the dosage form coating suspension can include: 1) stirring a desired amount of solvent at a level sufficient to generate a vortex; 2) adding a desired amount of the dosage form coating composition; and 3) mixing until a suspension forms.

The present disclosure provides a method of using a dosage form coating composition and/or suspension.

In cases where the dosage form coating composition is the starting material, the method of using the dosage form coating composition can include preparing a dosage form coating suspension having a solids content as described elsewhere herein. The method can then continue with the method described below with respect to the dosage form coating suspension.

In cases where the dosage form coating suspension is the starting material, the method of using the dosage form coating suspension can include applying the dosage form coating suspension to a plurality of uncoated dosage forms. As used herein, "uncoated" refers to a dosage form that has not had this specific coating applied. It is possible that a preliminary or base coating is applied to the dosage form prior to applying the dosage form coating suspension. The applying can be by spray coating. The method can include applying the dosage form coating suspension to a weight gain of at least 3%, at least 4%, or at least 5% and at most 10%, at most 9%, at most 8%, at most 7%, at most 6%, or at most 5%. It should be appreciated that the methods of using the dosage form coating suspension or the dosage form coating composition describe a broader range of weight gains than the weight gain range described with respect to the enteric properties achievable by the compositions and coatings described herein.

EXAMPLES

Materials

Pectin used in the following Comparative Examples and Examples was GENU® Pectin Type LM-22 GC, available commercially from CPKelco, Atlanta, Ga.

Sodium Alginate used in the following Comparative Examples and Examples was Ultra Low Viscosity Sodium Alginate, available commercially from Qingdao Hyzlin Biology Development Co., Ltd., Qingdao, China.

Comparative Example 1

| Ingredient | % by weight |
|---|---|
| Sodium Alginate | 10.80% |
| Glycerine | 1.20% |
| Deionized Water | 88.00% |

The formulation shown in Comparative Example 1 was prepared and had a viscosity between 300 and 600 cps at 12% solids.

Comparative Example 2

| Ingredient | % by weight |
| --- | --- |
| Pectin | 5.71% |
| Glycerine | 1.09% |
| Deionized Water | 93.20% |

The formulation shown in Comparative Example 2 was prepared and had a viscosity between 3300 and 3800 cps at 6.8% solids.

Comparative Example 3

| Ingredient | % |
| --- | --- |
| Sodium Alginate | 10.44% |
| Hydroxypropyl methyl cellulose (HPMC) | 4.86% |
| Glycerine | 2.70% |
| Deionized Water | 82.00% |

The formulation shown in Comparative Example 3 was prepared and had a viscosity between 300 and 500 cps at 18% solids.

Comparative Example 4

| Ingredient | % |
| --- | --- |
| Sodium Alginate | 6.70% |
| Pectin | 1.03% |
| Steric Acid | 0.72% |
| Glycerine | 1.55% |
| Deionized Water | 90.00% |

The formulation shown in Comparative Example 4 was prepared and had a viscosity between 300 and 500 cps at 10% solids.

Example 1

| Ingredient | % |
| --- | --- |
| Sodium Alginate | 5.00% |
| Pectin | 3.40% |
| Sunflower Lecithin | 0.30% |
| Coconut Oil | 1.30% |
| Deionized Water | 90.00% |

The formulation shown in Example 1 was prepared and had a viscosity between 300 and 1000 cps at 10% solids.

Example 2

| Ingredient | % |
| --- | --- |
| Sodium Alginate | 5.75% |
| Pectin | 2.40% |
| Sunflower Lecithin | 0.30% |
| Glycerine | 1.55% |
| Deionized Water | 90.00% |

The formulation shown in Example 2 was prepared and had a viscosity between 300 and 1000 cps at 10% solids.

Example 3

The compositions of Comparative Examples 1-4 and Examples 1 and 2 were applied to 1100 mg uncoated fish oil soft gels via spray coating using a Vector LDCS Hi-Coater, available commercially from Freund-Vector Corporation, Cedar Rapids, Iowa, USA. The coated soft gels were subjected to the disintegration method described in US Pharmacopeia 32 chapter <2040>, described above. A Sotax DT2 disintegration testing apparatus (available commercially from Sotax Corporation, Westborough, Mass.) was used for these tests.

With the coating made by Comparative Example 1, after 20 minutes in simulated gastric fluid, 6/6 of the coated soft gels had ruptured and began disintegrating. Thus, Comparative Example 1 does not produce an enteric coating. This suggests that the alginate and plasticizer alone are inadequate to form the enteric coating.

With the coating made by Comparative Example 2, after less than 10 minutes in simulated gastric fluid, 6/6 of the coated soft gels had ruptured and began disintegrating. Thus, Comparative Example 2 does not produce an enteric coating. This suggests that the pectin and plasticizer alone are inadequate to form the enteric coating.

With the coating made by Comparative Example 3, after 15-20 minutes in simulated gastric fluid, 6/6 of the coated soft gels had ruptured and began disintegrating. Thus, Comparative Example 3 does not produce an enteric coating. This suggests that utilizing the alginate and plasticizer with a cellulosic film forming polymer is inadequate to form the enteric coating.

With the coating made by Comparative Example 4, after 20 minutes in simulated gastric fluid, 6/6 of the coated soft gels had ruptured and began disintegrating. Thus, Comparative Example 4 does not produce an enteric coating. This suggests that not all concentrations and ratios of alginate and pectin are suitable for forming an enteric coating.

With the coating made by Example 1, after 60 minutes in simulated gastric fluid, 6/6 of the coated soft gels had not ruptured. The coated soft gels were then transferred to a beaker with simulated intestinal fluid pre-warmed to 37° C. Within the first few minutes in the simulated intestinal fluid, the soft gel coating split and disintegration of the soft gels followed rapidly. Thus, Example 2 produced an enteric coating. This suggests that a properly tailored composition, such as the one disclosed and claimed herein, can be suitable for forming an enteric coating.

With the coating made by Example 2, after 60 minutes in simulated gastric fluid, 6/6 of the coated soft gels had not ruptured. The coated soft gels were then transferred to a beaker with simulated intestinal fluid pre-warmed to 37° C. Within the first few minutes in the simulated intestinal fluid, the soft gel coating split and disintegration of the soft gels followed rapidly. Thus, Example 2 produced an enteric coating. This suggests that a properly tailored composition, such as the one disclosed and claimed herein, can be suitable for forming an enteric coating.

The particular aspects disclosed above are illustrative only, as the technology may be modified and practiced in different but equivalent manners apparent to those skilled in the art having the benefit of the teachings herein. Furthermore, no limitations are intended to the details of construction or design herein shown, other than as described in the claims below. It is therefore evident that the particular aspects disclosed above may be altered or modified and all such variations are considered within the scope and spirit of the technology. Accordingly, the protection sought herein is as set forth in the claims below.

We claim:

1. A dosage form coating composition comprising:
an alginate in an amount by weight of at least 40.0% and at most 80.0%;
a pectin in an amount by weight of at least 16.0% and at most 40.0%; and
a plasticizer in an amount by weight of at least 0.5% and at most 30.0%;
wherein the dosage form coating composition, when applied to a dosage form to a 3% to 5% weight gain, provides a coated dosage form having an enteric coating and at least the following two sequentially observed properties:
(i) the enteric coating does not exhibit visible signs of dissolution after being immersed in a 0.1 M solution of hydrochloric acid or simulated gastric fluid at a predetermined temperature and for a first predetermined length of time, wherein the predetermined temperature is between 30° C. and 45° C., wherein the first predetermined length of time is between 15 minutes and 3 hours; and
(ii) after the being immersed in the 0.1 M solution of hydrochloric acid or simulated gastric fluid, the enteric coating is at least partially dissolved after being immersed in a phosphate buffer having a pH between 6.5 and 7.0 or simulated intestinal fluid at the predetermined temperature for a second predetermined length of time, wherein the second predetermined length of time is between 60 minutes and 6 hours.

2. The dosage form coating composition of claim 1, wherein the alginate and the pectin are present in a weight ratio of between 1:1 and 5:1.

3. The dosage form coating composition of claim 1, the dosage form coating composition comprising an emulsifying agent.

4. The dosage form coating composition of claim 3, wherein the emulsifying agent is a lecithin.

5. The dosage form coating composition of claim 4, wherein the lecithin is a sunflower lecithin.

6. The dosage form coating composition of claim 3, wherein the emulsifying agent is present in an amount by weight of between 0.1% and 10.0%.

7. The dosage form coating composition of claim 1, wherein the alginate is present in an amount by weight of between 45.0% and 80%.

8. The dosage form coating composition of claim 1, wherein the alginate is sodium alginate.

9. The dosage form coating composition of claim 1, wherein the alginate has a viscosity as measured at 10% solids of between 1 cP and 500 cP.

10. The dosage form coating composition of claim 1, wherein the pectin is present in an amount by weight of between 17.0% and 40.0%.

11. The dosage form coating composition of claim 1, wherein the pectin has a degree of esterification of between 40% and 55%.

12. The dosage form coating composition of claim 1, wherein the pectin is non-amidated.

13. The dosage form coating composition of claim 1, wherein the plasticizer is present in an amount by weight of between 2.5% and 30.0%.

14. The dosage form coating composition of claim 1, wherein the plasticizer is at least one of glycerine or coconut oil.

15. The dosage form coating composition of claim 1, wherein the predetermined temperature is between 35° C. and 39° C.

16. The dosage form coating composition of claim 1, the dosage form coating composition further comprising at least one of an opacifying agent, a sweetening agent, a flavor masking agent, a colorant, a spray dried flavorant, a dried crystal flavorant, a liquid flavorant, a granule flavorant, a spray dried sensate, a dried crystal sensate, a granule sensate, or a liquid sensate.

17. The dosage form coating composition of claim 1, wherein the composition is substantially free of cellulosic film formers.

18. The dosage form coating composition of claim 1, wherein the composition is substantially free of shellac.

19. The dosage form coating composition of claim 1, wherein the composition is substantially free of modified food starch.

20. A dosage form coating composition comprising:
an alginate in an amount by weight of at least 40.0% and at most 80.0%;
a pectin; and
a plasticizer;
wherein the alginate and the pectin are present in a weight ratio of at least 1:1 and at most 5:1, wherein the dosage form coating composition, when applied to a dosage form to a 3% to 5% weight gain, provides a coated dosage form having an enteric coating and at least the following two sequentially observed properties:
(i) the enteric coating does not exhibit visible signs of dissolution after being immersed in a 0.1 M solution of hydrochloric acid or simulated gastric fluid at a predetermined temperature and for a first predetermined length of time, wherein the predetermined temperature is between 30° C. and 45° C., wherein the first predetermined length of time is between 15 minutes and 3 hours; and
(ii) after the being immersed in the 0.1 M solution of hydrochloric acid or simulated gastric fluid, the enteric coating is at least partially dissolved after being immersed in a phosphate buffer having a pH between 6.5 and 7.0 or simulated intestinal fluid at the predetermined temperature for a second predetermined length of time, wherein the second predetermined length of time is between 60 minutes and 6 hours.

* * * * *